(12) United States Patent
Pang et al.

(10) Patent No.: US 10,327,704 B2
(45) Date of Patent: Jun. 25, 2019

(54) DRY BONDING SYSTEM AND WEARABLE DEVICE FOR SKIN BONDING INCLUDING THE SAME

(71) Applicant: RESEARCH & BUSINESS FOUNDATION SUNGKYUNKWAN UNIVERSITY, Suwon-si (KR)

(72) Inventors: Changhyun Pang, Seoul (KR); Young Jin Park, Seoul (KR); Sang Yul Baik, Seosan-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 654 days.

(21) Appl. No.: 14/982,475

(22) Filed: Dec. 29, 2015

(65) Prior Publication Data

US 2016/0206243 A1    Jul. 21, 2016

(30) Foreign Application Priority Data

Dec. 29, 2014  (KR) .................. 10-2014-0192195
Aug. 28, 2015  (KR) .................. 10-2015-0121757
Dec. 24, 2015  (KR) .................. 10-2015-0186115

(51) Int. Cl.
*A61B 5/00* (2006.01)
*B32B 3/30* (2006.01)
*A61F 13/02* (2006.01)

(52) U.S. Cl.
CPC ........ *A61B 5/6834* (2013.01); *A61F 13/0253* (2013.01); *A61F 13/0256* (2013.01); *B32B 3/30* (2013.01)

(58) Field of Classification Search
None
See application file for complete search history.

(56) References Cited

U.S. PATENT DOCUMENTS

| 4,095,590 | A | * | 6/1978 | Harrigan | A61H 31/005 434/265 |
| 5,512,041 | A | * | 4/1996 | Bogart | A61F 13/023 428/40.1 |
| 2004/0081801 | A1 | * | 4/2004 | Albert | A41D 19/01558 428/159 |
| 2009/0137480 | A1 | * | 5/2009 | Stern | A61K 9/0021 514/8.1 |
| 2011/0076457 | A1 | * | 3/2011 | Reichwein | B32B 25/14 428/172 |
| 2012/0016308 | A1 | * | 1/2012 | Schott | A61B 5/151 604/173 |
| 2014/0180356 | A1 | * | 6/2014 | Shuros | A61N 1/0558 607/44 |

FOREIGN PATENT DOCUMENTS

KR    10-2007-0018410 A    2/2007

OTHER PUBLICATIONS

Tramacere et al. 2012 IEEE International Conference on Robotics and Automation p. 3846-3851 (Year: 2012).*
Tramacere et al. PLOS One 2013 8(6):e65074 p. 1-7 (Year: 2013).*
Bae, Won Gyu, et al. "Fabrication and Application of Smart Dry Adhesive Film Uisng Biomimetic", Jul. 2011, vol. 22(3), pp. 230-236. (9 pages, with English abstract).
Korean Office Action dated Nov. 17, 2016 in counterpart Korean Patent Application No. 10-2015-0186115 (7 pages, in Korean).

* cited by examiner

*Primary Examiner* — Robert A Wax
*Assistant Examiner* — Caralynne E Helm
(74) *Attorney, Agent, or Firm* — NSIP Law

(57) ABSTRACT

Disclosed are a dry bonding system and a wearable device for skin bonding including the dry bonding system.

14 Claims, 17 Drawing Sheets

[FIG. 1]
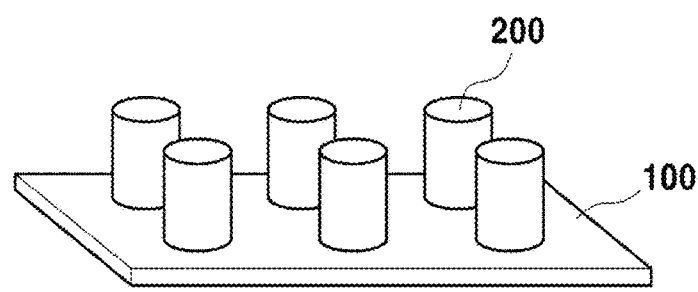
[FIG. 2]
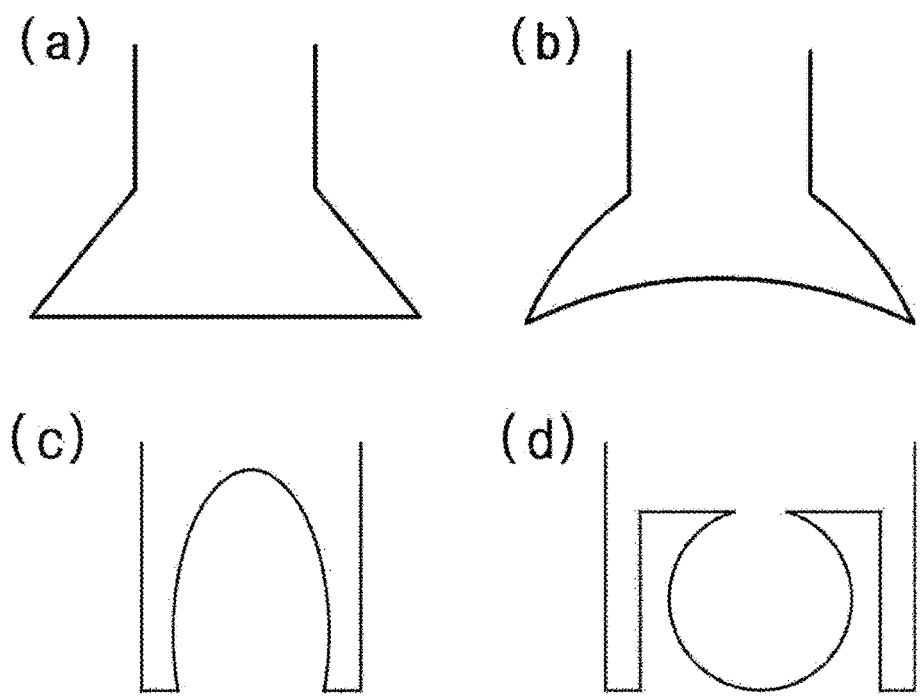

[FIG. 3]
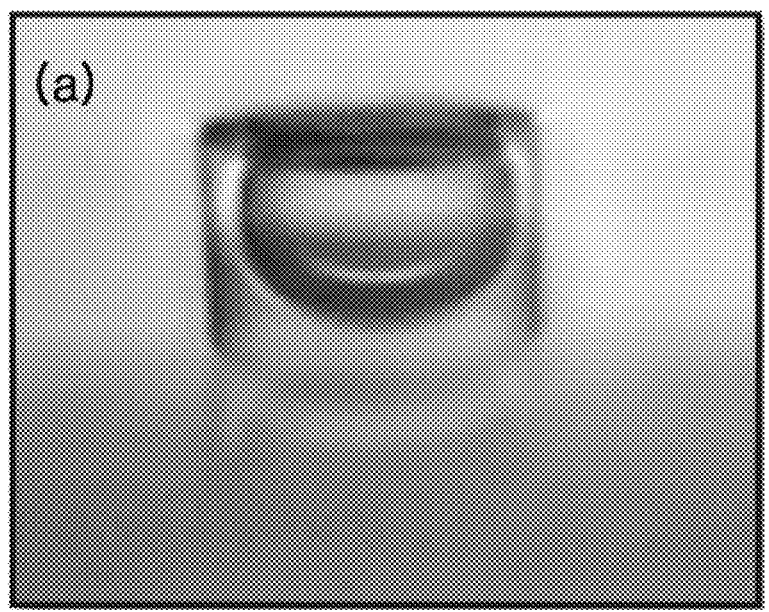
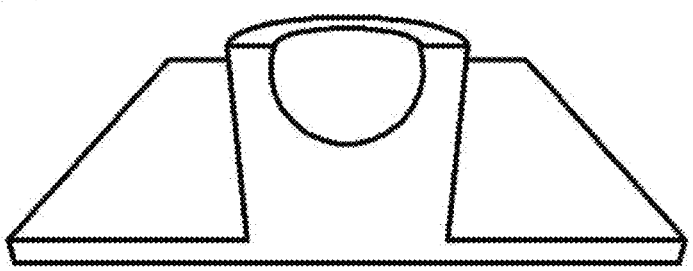

【FIG. 4】
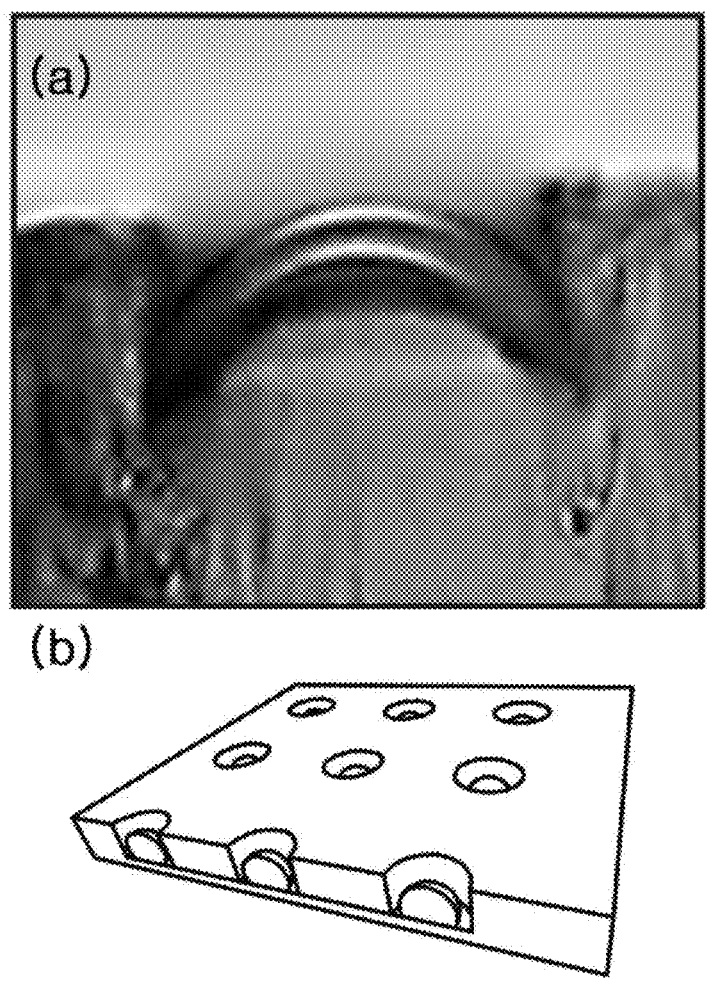
【FIG. 5】
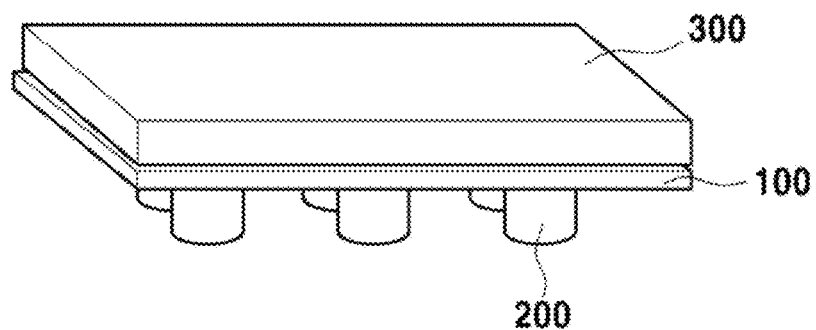

[FIG. 6]
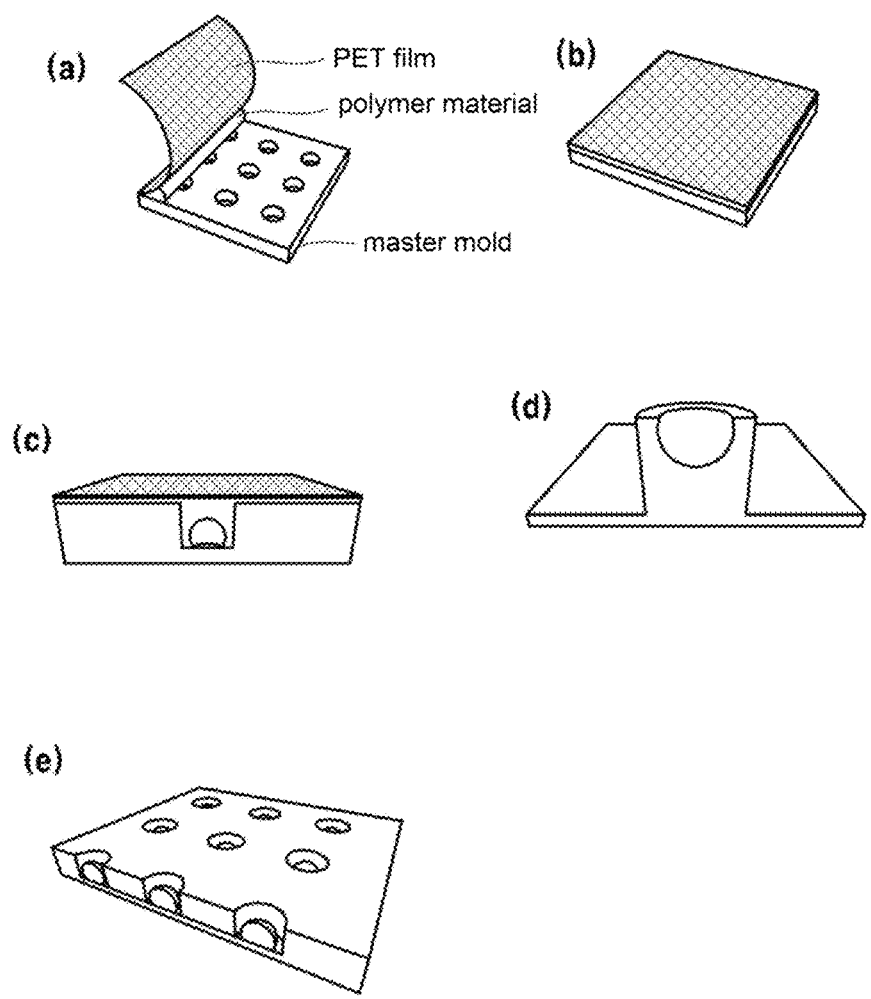

[FIG. 7]
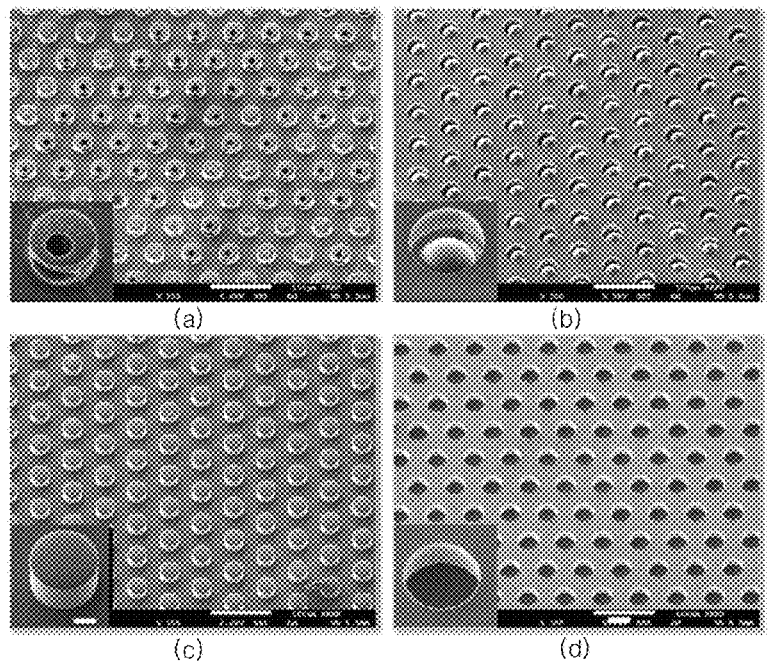
(a)  (b)
(c)  (d)
[FIG. 8a]
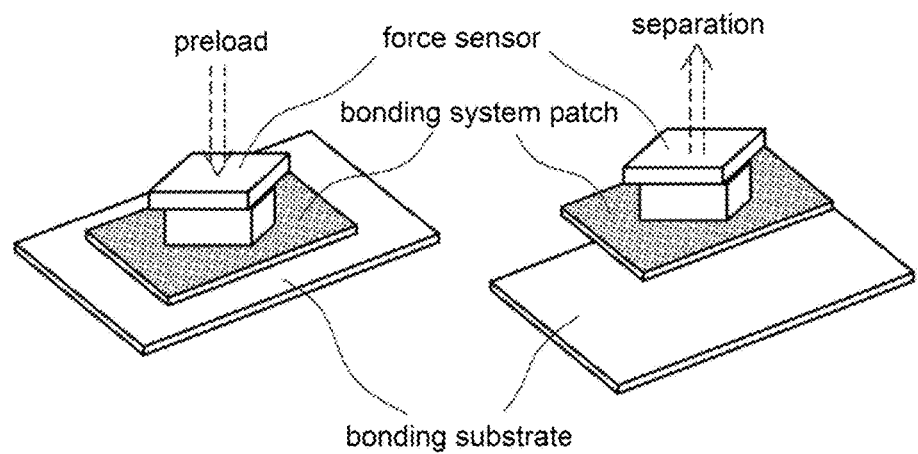

[FIG. 8b]
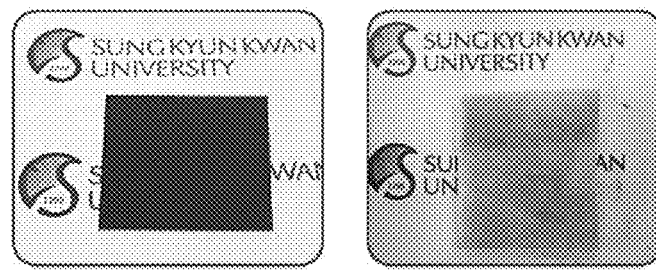

[FIG. 9]
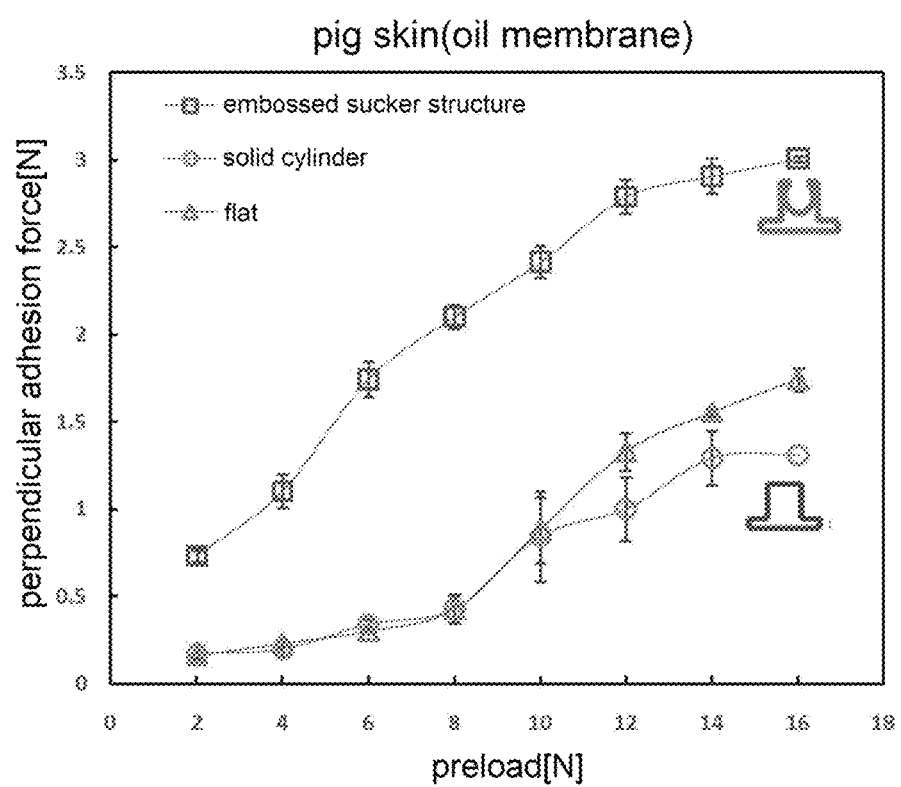

[FIG. 10]
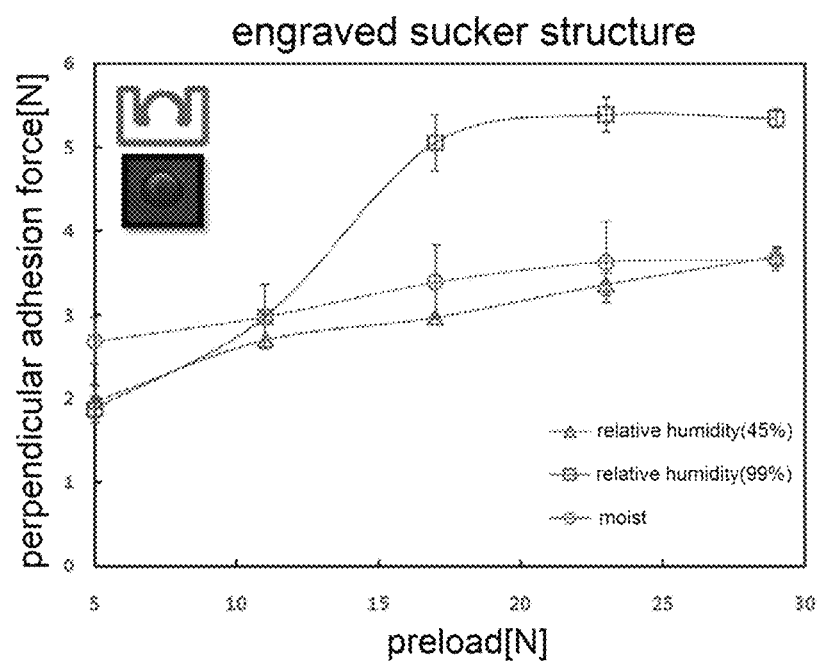

[FIG. 11a]
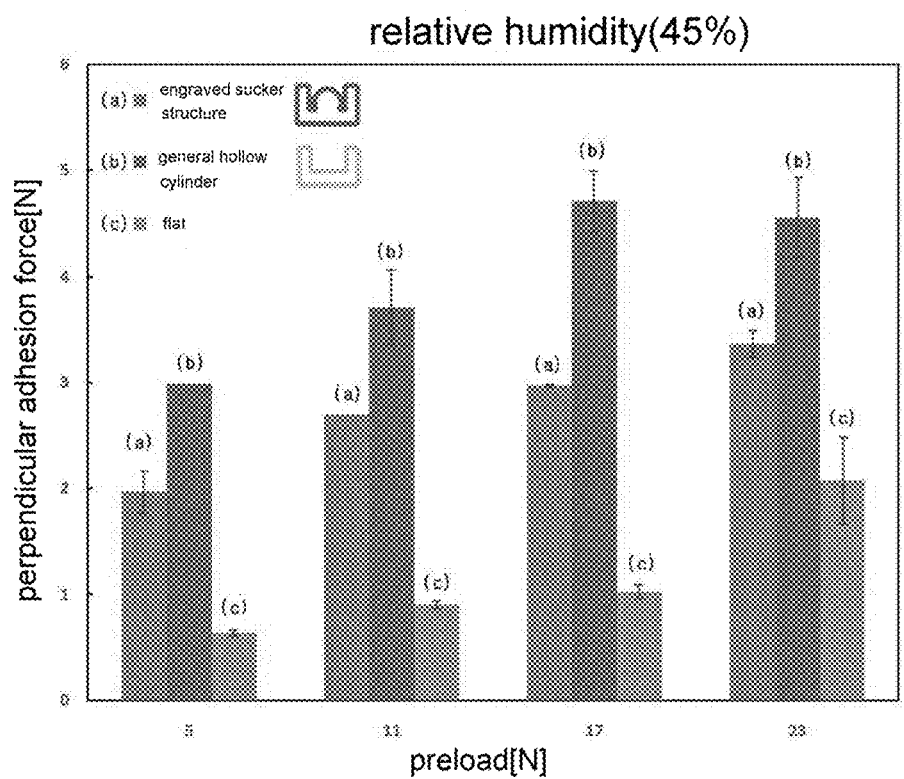

[FIG. 11b]
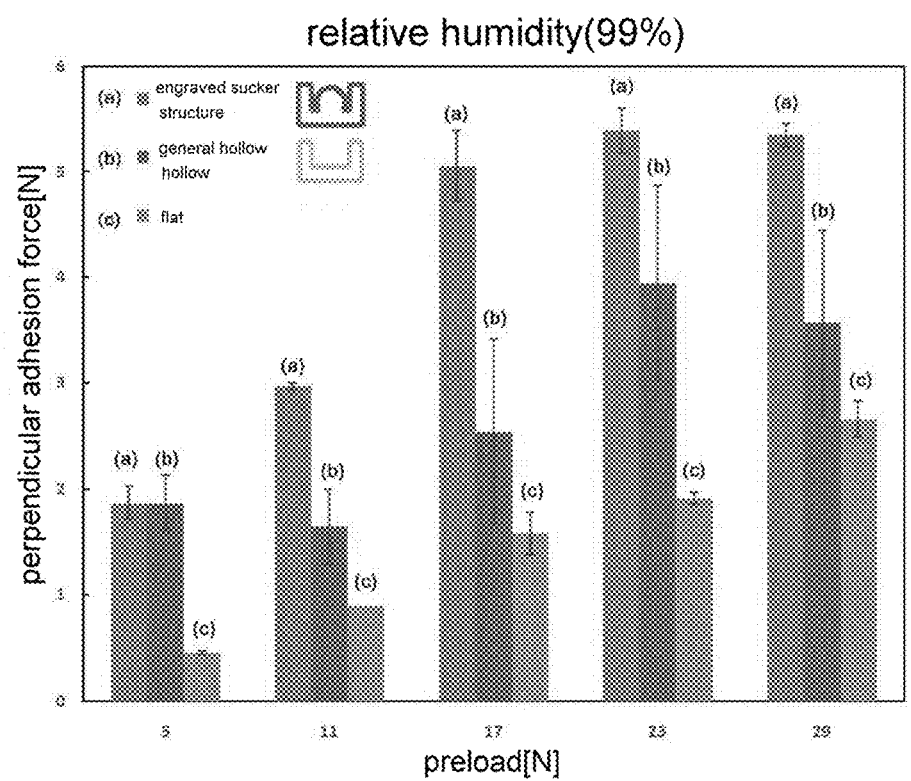

[FIG. 11c]
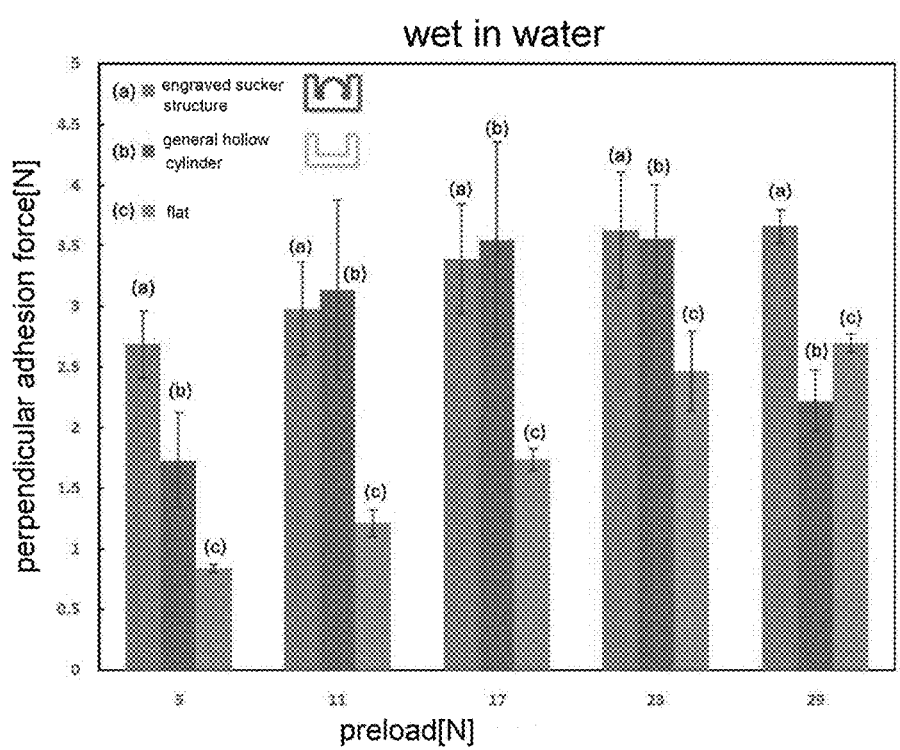

[FIG. 12a]
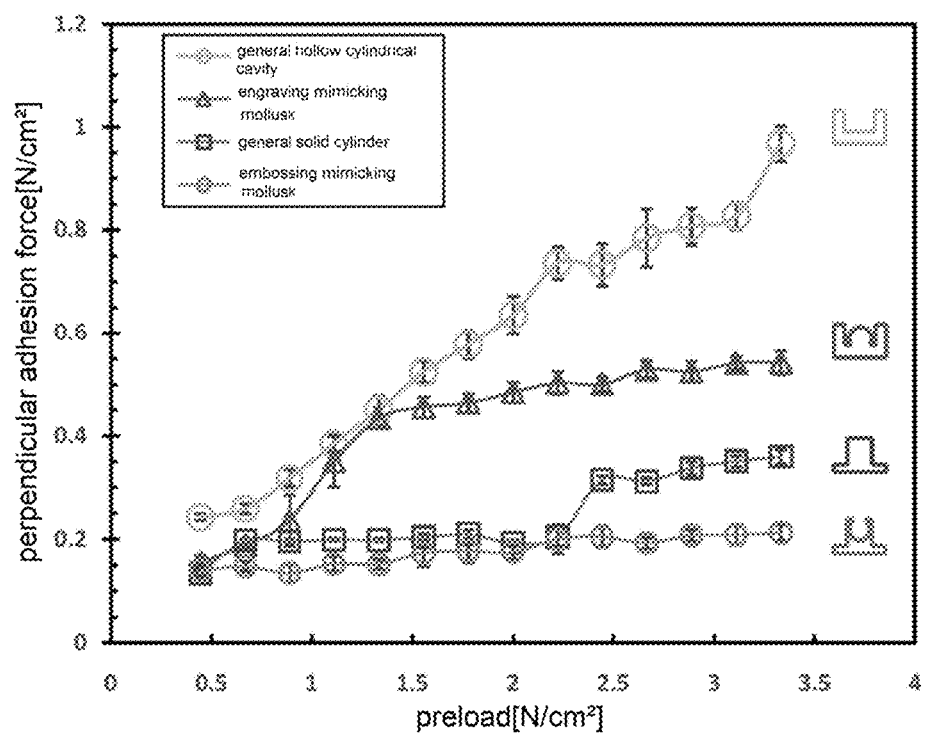

[FIG. 12b]
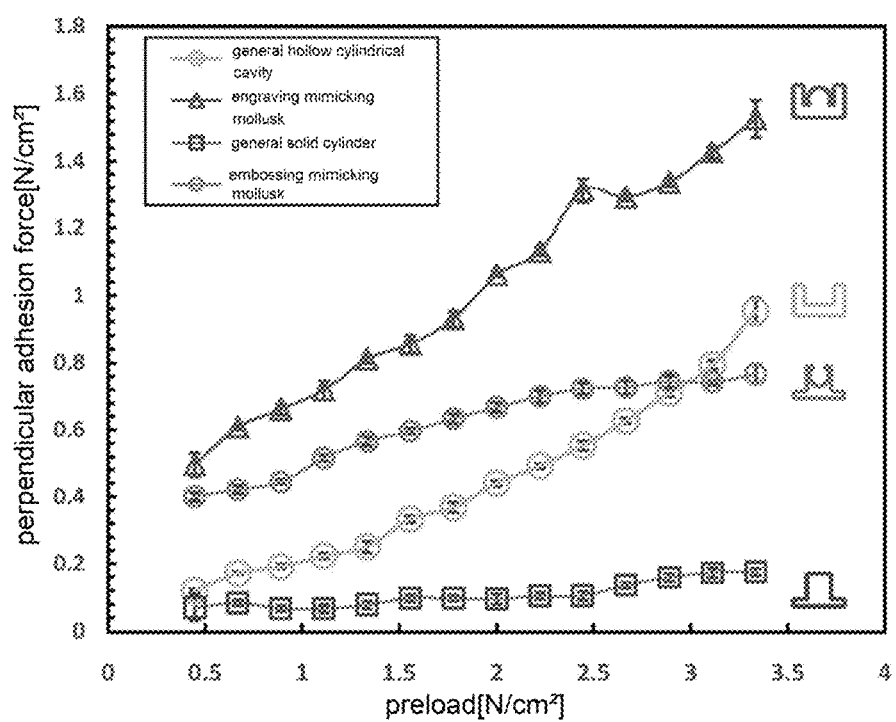

[FIG. 13a]
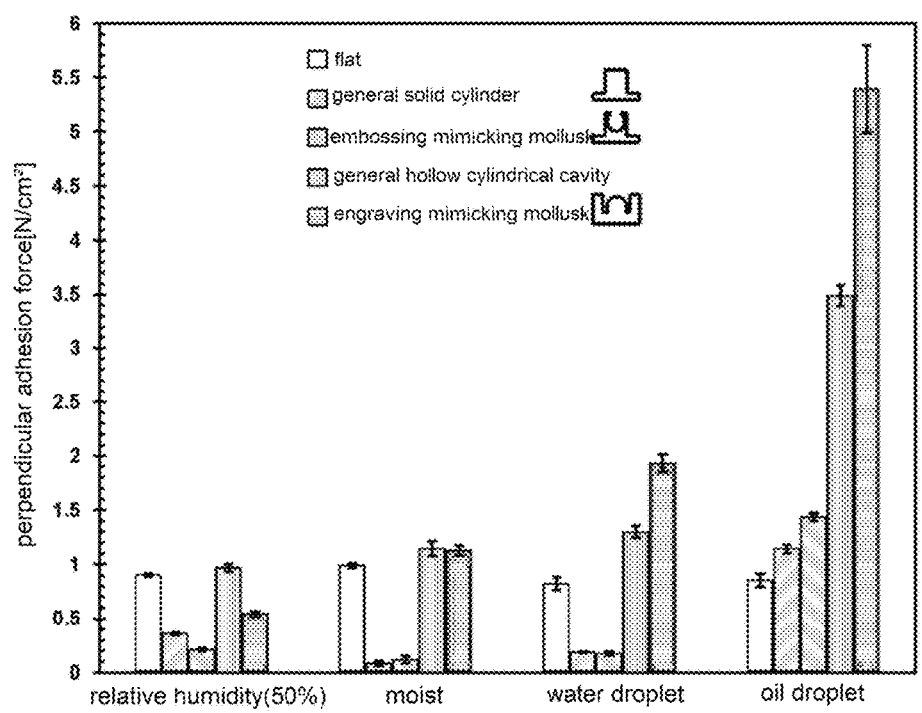

[FIG. 13b]
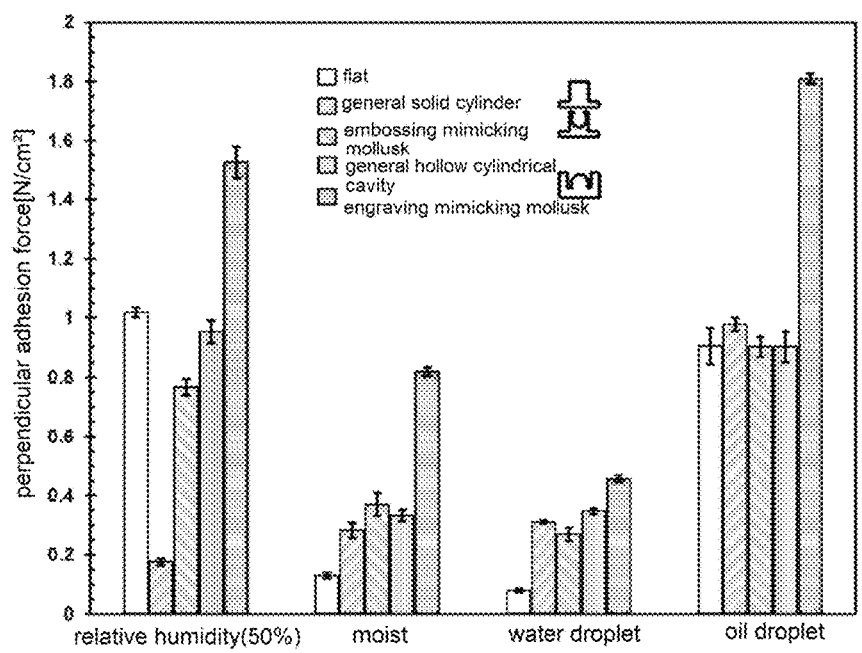

[FIG. 14a]
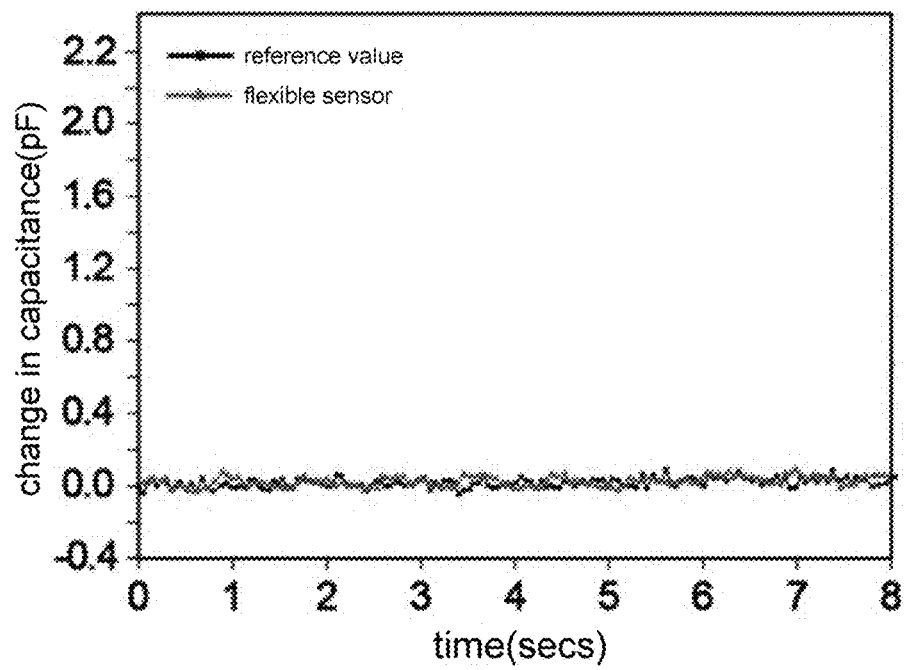

[FIG. 14b]
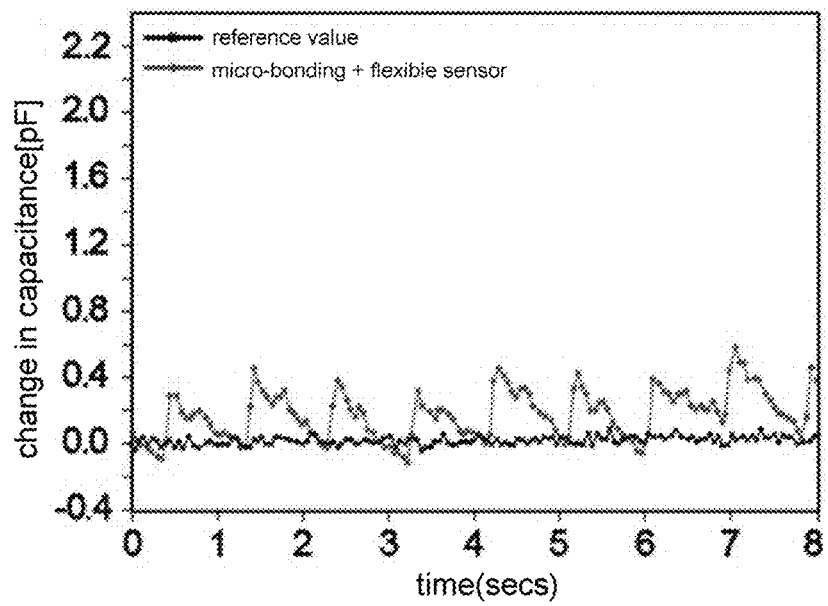
[FIG. 15]
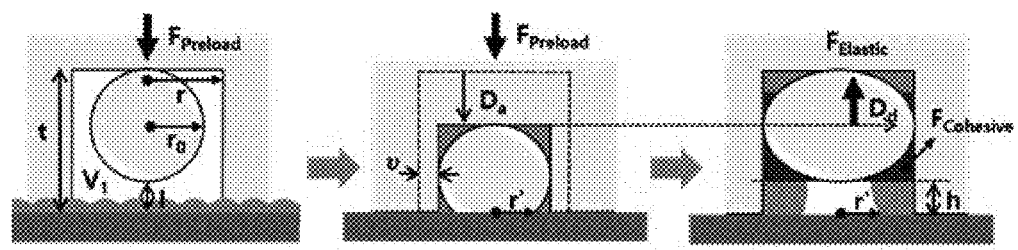

DRY BONDING SYSTEM AND WEARABLE DEVICE FOR SKIN BONDING INCLUDING THE SAME

CROSS-REFERENCE TO RELATED APPLICATIONS

This application claims the benefit of Korean Patent Application No. 10-2014-0192195 filed on Dec. 29, 2014 in the Korean Intellectual Property Office, Korean Patent Application No. 10-2015-0121757 filed on Aug. 28, 2015 in the Korean Intellectual Property Office, and Korean Patent Application No. 10-2015-0186115 filed on Dec. 24, 2015 in the Korean Intellectual Property Office, the entire disclosures of which are incorporated herein by reference for all purposes.

BACKGROUND

1. Field of the Invention

The present disclosure relates to a dry bonding system and a wearable device for skin bonding including the same.

2. Discussion of Related Art

Wearable devices are technology for clothing and accessories incorporating a computer and existing electronic technologies. Since the wearable device often interacts with a human body while in contact with the human body, various fields of sciences have been developed on an interface between the wearable device and the human body. According to this trend, there have been increasing demands and researches on a diagnosis wearable device that merges with a diagnosis device based on the virtue of a dry bonding technology. For example, there have been ongoing researches about application of the dry bonding technology in order to improve the stability and permeability that do not meet requirement for manufacturing a patch type sensor that measures a biometric signal, such as electrocardiogram and pulse, or manufacturing a cosmetic patch for beauty care, and further in order to amplify a biometric signal.

In nature, various mechanisms of bonding methods are present, for example, slime of a snail, protein of a hard-shelled mussel, insect wing joining, legs of a gecko lizard, legs a jumping spider, and seeds of thistle. Since the bonding systems in nature are significantly superior in the efficiency, various adhesives, such as an adhesive band for medical treatment, an adhesive tape, post-it and Velcro, are made to mimic the bonding systems in nature. However, in order to combine a ultra-sensitive patch type sensor to an object, the bonding method needs to satisfy the following requirements. First, a boning portion does not generate a great disturbance (noise) in a signal transmission process. Second, a sufficient adhesion force is ensured regardless of a curvature or roughness of a surface of the object to prevent the patch from being easily separated. In addition, attaching and detaching processes are easy, and the adhesion force is maintained in the mid of the processes. Finally, a surface of a measurement object is not damaged, and especially, in the case of the bonding method used for human skin, stimulus, contamination, or unpleasant sensation does not occur.

Therefore, a wet bonding method has constraints in the use since detachment requires a great force or leaves some scars or skin troubles, and adhesion force is lowered in a repeated use. In this context, a bio-inspired dry bonding system is considered as a dry adhesive capable of achieving repeated attachment/detachment without leaving contamination and damage on a surface of an object based on interaction of fine ciliary, and thus studied in various fields.

However, the bio-inspired bonding system has an adhesion force which does not reach a predetermined level corresponding to the existing medical wet tape. In addition, as for a wearable sensor for skin bonding, various technical concepts have been reported, but there is need of studies on the permeability and bonding issues at an interface between a device and a skin.

To take the ultra-sensitive sensor for skin bonding and the dry medical adhesive for optimizing biometric signal detection as a representative example of the above study, first, there is an overseas research (Nature Communication 4:1702), conducted by Yang Seung-Yun's research team in a Harvard medical school based on bio-mimicking the shape of a micro needle of a cactus. However, this method has insufficient adhesion force and limitation in application of an ultrasensitive sensor.

In the second example, Karp's research team in Harvard Medical school has studied a skin patch which is attached to a medical device, a study on a medical tape with regard to easy separation of a patch and prevention of skin damage by using bio-mimicking a spider web system. However, this method shows a lower adhesion force compared to the existing adhesive, and related researches are only focused on the separation of a patch.

The third method involves a reversible electric connector using interlocking of fine ciliary, a multifunctional sensor using the same, and a method of manufacturing a sensor having multiple functions using the same (Korean Unexamined Patent Application Publication No. 10-2011-0050382) which suggests a reversible electric connector that can maximize the efficiency of electricity by connecting electrodes using a bio-inspired nanoscale structure to minimize generation of resistance and also suggests a multifunctional sensor having the nanoscale structure that can respond to a small pressure and small force in a delicate manner and provide a great sensitivity reacting to a small change. However, when two nanostructure surfaces are bonded to implement nanoscale interlocking, the bonding lacks an adhesive function that is required for application of a diagnosis wearable device.

The fourth method, referred to as Epidermal Electronics, developed by University of Illinois at Urbana-Champaign, involves a wearable sensor for skin bonding in which a pattern is attached to a skin using a LAP ON A CHIP or a patch type sensor system, which is thin and bendable unlike an existing wafer based chip, through a tattoo scheme. However, this technology is complicated in the manufacturing and the structure so that practical use is limited. In addition, the use of the tattoo bonding system may cause reluctance to skin bonding and weakness in the permeability and stability.

Finally, there is a research by a School Shanghai Jiao Tong University research team, conducted on a medical skin patch that is configured to measure electrocardiogram (ECG) by merging a dry bonding skin patch with a dry electrode based on a mushroom shape biomimicking. However, this method shows a weak bonding structure against a shear stress, and thus not sufficient for being applied to a skin patch.

To summarize, various researches and developments are present about the ultrasensitive sensor technology and the dry bonding system, but still have limitation on the technical performance, and leaves much to be done in merging the ultrasensitive sensor technology and the dry bonding system to manufacture a diagnosis wearable device.

SUMMARY OF THE INVENTION

The present disclosure is directed to technology for a dry bonding system and a wearable device for skin bonding including the same.

The technical objectives of the inventive concept are not limited to the above disclosure; other objectives may become apparent to those of ordinary skill in the art based on the following descriptions.

In accordance with one aspect of the present disclosure, there is provided a dry bonding system including a plurality of micro structures each having a sucker chamber formed on a substrate.

The dry bonding represents a bonding method not using a chemical adhesive.

The sucker chamber is provided in a shape having a cavity recessed in the form of an octopus's sucker, such that, when a circumference of an upper most end of the sucker is attached to a surface to be bonded, air leakage is prevented so as to cause a pressure difference between inside and outside of the sucker.

The micro structure includes a material selected from the group consisting of polyurethaneacrylate (PUA), polydimethylsiloxane (PDMS), polyethyleneterephthalate (PET), polyurethane, polyethylenenaphthalate (PEN), and a combination thereof.

The adhesion force represents a van der Waals force with respect to a surface to be bonded; or a suction force caused by a pressure difference between inside and outside of a sucker due to a change of the shape of the sucker.

The micro structure includes an embossed structure, and the sucker chamber is formed at an upper end of the embossed structure.

The embossed structure represents a structure denoted as reference numeral 200 in FIG. 2, and may be provided in the form of a bar protruding from a substrate. In this case, the embossed structure may have a cavity as shown in (b) of FIG. 3, and the embossed structure serves as a sucker.

The micro structure according to the present disclosure is characterized in having a hill-shaped embossed part at a base surface of the sucker chamber. The base surface represents a bottom surface of the cavity space, and the hill-shaped embossed part represents a spherical protrusion as shown in (d) of FIG. 2.

Alternatively, the micro structure is an engraved structure carved in a surface of the substrate, and the engraved structure is a sucker chamber.

The engraved structure may represent an engraved column shape carved into the substrate as shown in (b) of FIG. 7. The engraved recess is a cavity serving as a sucker.

The sucker chamber is provided at a base surface thereof with a hill-shaped embossed part, and the hill-shaped embossed part has a height smaller than a depth of the sucker.

The hill-shaped embossed part provides a superior adhesion force compared to a bonding system not having a hill-shaped embossed part. The sucker of the present disclosure causes a change in shape (that is, a change in volume) according to a force applied to a rear surface of the bonding system when the sucker is attached to a surface to be bonded, and thus a suction force is provided, and the change in volume may be significantly increased. In addition, a surface generating a capillary force due to moisture existing on a surface to be bonded at the bonding process is larger compared to a bonding system not having an embossed part, and the capillary force may be increased. Therefore, in the case of attachment in a wet environment, for example, attachment to a liquid drug coating surface or attachment at discharge of body secretion, a superior adhesion force is provided.

In particular, the embossed part has a height smaller than the depth of the sucker chamber. If the embossed part has a height larger than the depth of the sucker chamber, the sucker may not work.

The hill-shaped embossed part is formed such that a middle portion of a body of the hill-shaped embossed part has a circumference larger than circumferences of an upper end and a lower end of the body. The hill-shaped embossed part may be provided in the form of a sphere or in the form of a sphere-like shape larger than a semi-sphere.

A circumference of the hill-shaped embossed part is smaller than a circumference of the sucker chamber, and when the hill-shaped embossed part is attached to a surface to be bonded and a pressure for adsorption of the sucker chamber is not applied to a rear surface of the bonding system, a maximum circumferential surface of the hill-shaped embossed part does not come into contact with the circumference of the sucker chamber, and when the hill-shaped embossed part is attached to the surface to be bonded and a pressure for adsorption of the sucker chamber is applied to the rear surface of the bonding system, the maximum circumferential surface of the hill-shaped embossed part comes into contact with an inner surface of the sucker chamber.

Referring to the left side drawing of FIG. 15, when the hill-shaped embossed part having a spherical shape is attached to a surface to be bonded and a pressure is not applied to the rear surface of the bonding system, the embossed part does not come into contact with the surface to be bonded and the inner surface of the sucker chamber. Referring to the middle of FIG. 15, when a pressure is applied to the rear surface, the maximum circumferential surface of the hill-shaped embossed part comes into contact with the inner surface of the sucker chamber, and in particular, upon stopping of pressing the rear surface in a wet environment, the circumferential surface and the inner surface of the sucker chamber maintains the contact and physically separates a space between the surface to be bonded and the contact surface from a space between the contact surface and the base surface, and a liquid moves to the contact surface and base surface to cause a pressure difference, so that a suction is maintained due to the pressure difference and a strong adhesion is maintained.

The embossed structure is provided in the form of a cylinder, and the hill-shaped embossed part is provided in the form of a sphere or semi-sphere protruding from the base surface.

The embossed structure has a diameter of about 1 μm to 100 μm and has a height of about 1 μm to 100 μm, and an aspect ratio of the diameter to the height of the embossed structure is within a range of ⅔ to 3.

An adhesion force converges at a diameter of 100 μm, and thereafter, decreases.

The plurality of micro structures are arranged while spaced apart each other at an interval whose ratio with respect to a diameter of the sucker chamber is within a range of 1:1 to 1:3.

In accordance with another aspect of the present disclosure, there is provided a wearable device for skin bonding including a sensor part and a bonding part provided at an opposite side of the sensor part, wherein the bonding part includes the dry bonding system described above.

In accordance with still another aspect of the present disclosure, there is provided a skin bonding patch including the dry bonding system described above, wherein the skin bonding patch is used in a wet environment. The skin bonding patch may include a moist wound healing dressing.

In accordance with yet another aspect of the present disclosure, there is provided a drug delivery bonding patch including the dry bonding system described above, wherein the dry bonding system includes a drug loaded into the sucker chamber.

As is apparent from the above, the dry bonding system according to an exemplary embodiment of the present disclosure is combined with various high sensitivity sensors, thereby realizing a wearable device for skin bonding that can ensure a sufficient adhesion force on various surfaces, a durability after the attachment, and superiority in repeated attachment and detachment. In addition, the dry bonding system according to an exemplary embodiment of the present disclosure is easy to be manufactured in a large size, and the wearable device for skin bonding including the dry bonding system, when attached to a skin, can minimize contamination or irritation on the skin in contact.

In addition, according to an exemplary embodiment of the present disclosure, a dry bonding system that mimics a bonding system of a mollusk, such as an octopus, is used so that the suction effect allows the adhesion force to be maintained even at a high humidity or even if a surface is wet.

According to an exemplary embodiment of the present disclosure, a fine signal is amplified by using the wearable device for skin bonding, so as to measure a biometric signal that is difficult to be measured with the existing sensor technology, thereby improving the accuracy in diagnosing physical diseases. In addition, the wearable device for skin bonding according to an exemplary embodiment of the present disclosure can be used in diagnosing mental diseases.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 1 is a schematic diagram illustrating a dry bonding system according to an exemplary embodiment of the present disclosure;

FIG. 2(a) to (d) are schematic diagrams illustrating a micro structure having a sucker shape according to an exemplary embodiment of the present disclosure;

FIGS. 3(a) and (b) are an optical microscopic image and a schematic diagram of a section of a dry bonding system having an embossed sucker structure according to an exemplary embodiment of the present disclosure;

FIGS. 4(a) and (b) are an optical microscopic image and a schematic diagram illustrating a section of a dry bonding system having an engraved sucker structure according to an exemplary embodiment of the present disclosure;

FIG. 5 is a schematic diagram illustrating a wearable device for skin bonding according to an exemplary embodiment of the present disclosure;

FIG. 6(a) to (e) illustrate a flowchart showing a method of manufacturing a dry bonding system according to an exemplary embodiment of the present disclosure;

FIG. 7(a) to (d) are SEM images illustrating dry bonding systems respectively having an embossed sucker structure, an engraved sucker structure, a solid cylindrical structure and a hollow cylindrical structure according to exemplary embodiments of the present disclosure;

FIGS. 8A and 8B are schematic diagrams respectively illustrating an experiment on an adhesion force in a perpendicular direction and a bonding substrate of a bonding system according to an exemplary embodiment of the present disclosure;

FIG. 9 is a graph showing a result of measuring a perpendicular adhesion force when an oil membrane exists on a surface according to an exemplary embodiment of the present disclosure;

FIG. 10 is a graph showing a result of measuring a perpendicular adhesion force at different humidity environments according to an exemplary embodiment of the present disclosure;

FIGS. 11A to 11C are graphs each showing a comparison result of perpendicular adhesion force measurement at each humidity according to an exemplary embodiment of the present disclosure;

FIGS. 12A and 12B are graphs each showing a result of measuring a perpendicular adhesion force of a dry bonding system according to an exemplary embodiment of the present disclosure;

FIGS. 13A and 13B are graphs respectively showing a result of measuring a perpendicular adhesion force of a dry bonding system according to an exemplary embodiment of the present disclosure and a result of measuring a perpendicular adhesion force of a dry bonding system according to a comparative example, under various environments;

FIGS. 14A and 14B are graphs showing a signal amplification effect of a wearable device including a dry bonding system according to an exemplary embodiment of the present disclosure; and FIG. 15 is a diagram illustrating a dry bonding system according to an exemplary embodiment of the present disclosure being used in a moist environment.

DETAILED DESCRIPTION OF EXEMPLARY EMBODIMENTS

Hereinafter, illustrative embodiments and examples of the present disclosure will be described in detail with reference to the accompanying drawings so that the present disclosure may be readily implemented by those skilled in the art. However, it is to be noted that the present disclosure may not be limited to the illustrative embodiments and examples but can be embodied in various other ways. In drawings, parts irrelevant to the description are omitted for the simplicity of explanation, and like reference numerals denote like parts throughout the whole document.

Throughout the whole document, the term "connected to" or "coupled to" that is used to designate a connection or coupling of one element to another element includes both a case that an element is "directly connected or coupled to" another element and a case that an element is "electronically connected or coupled to" another element via still another element.

Throughout the whole document, the term "on" that is used to designate a position of one element with respect to another element includes both a case that the one element is adjacent to the another element and a case that any other element exists between these two elements Throughout the whole document, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Throughout the whole document, the term "step of" does not mean "step for".

Throughout the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the whole document, the term "A and/or B" means "A or B or A and B".

Hereinafter, the present disclosure will be described in detail with reference to the accompanying drawings.

FIG. 1 is a schematic diagram illustrating a dry bonding system according to the present disclosure.

Referring to FIG. 1, a dry bonding system according to an exemplary embodiment of the present disclosure includes a plurality of micro structures 200 formed on a substrate 100.

According to an exemplary embodiment of the present disclosure, the micro structure 200 may include a sucker shape. According to an exemplary embodiment of the present disclosure, the micro structure 200 having a sucker shape is obtained by mimicking a bonding system of a mollusk, such as an octopus, and the shape of a sucker may be provided in a size of nanoscales or micro scales.

According to an exemplary embodiment of the present disclosure, the micro structure 200 may include a solid cylindrical shape or a cylindrical hollowness shape, or an embossed shape having a three dimensional structure or an engraved shape having a three dimensional structure.

According to an exemplary embodiment of the present disclosure, the micro structure 200 having a three dimensional structure may include an embossed shape as shown in drawings (a) and (b) of FIG. 3.

According to an exemplary embodiment of the present disclosure, the micro structure 200 having a three dimensional structure may include an engraved shape as shown in drawings (a) and (b) of FIG. 4. In particular, as shown in drawing (b) of FIG. 4, a semi-spherical embossed part may be provided in an engraved cavity.

According to an exemplary embodiment of the present disclosure, a material forming the substrate 100 is not limited as long as it allows the micro structure 200 to be formed on a surface of the substrate 100 by a patterning. For example, the material forming the substrate 100 may include an ultraviolet curable polymer or thermal curable polymer. For example, the substrate 100 may include a material selected from the group consisting of polyethyleneterephthalate (PET), polydimethylsiloxane (PDMS), polyurethane, polyurethaneacrylate, polyethylenenaphthalate (PEN) and a combination thereof.

According to an exemplary embodiment of the present disclosure, the micro structure 200 may include a material selected from the group consisting of polyurethaneacrylate (PUA), polydimethylsiloxane (PDMS), polyethyleneterephthalate (PET), polyurethane, polyethylenenaphthalate (PEN), and a combination thereof. According to an exemplary embodiment of the present disclosure, the micro structure 200 is manufactured by using a biocompatible polymer, such as PUA and PDMS, thereby achieving a durability such that the micro structure 200 may be repeatedly attached and detached without degrading the adhesion force.

According to an exemplary embodiment of the present disclosure, the dry bonding system may be manufactured by using a micro molding, but the manufacturing method thereof is not limited thereto. In detail, the dry bonding system may be manufactured by using a liquid-liquid phase separation. For example, the dry bonding system may be manufactured by coating a substrate with a first solution including polyol dissolved in a solvent, dewetting the first solution, evaporating the solvent, coating the substrate with a second solution including a biocompatible polymer, and separating the second solution through congelation.

According to an exemplary embodiment of the present disclosure, the adhesion force may represent a van der Waals force with respect to a surface to be bonded, a capillary force according to moisture existing on an interface to be bonded, and a suction force caused by a pressure difference between inside and outside of a sucker. The existing dry bonding mechanism operates dependent on a van der Waals force, but according to the present disclosure, a suction force caused by the sucker is added to a van der Waals force so that the adhesion strength is increased, and in addition, even in a moist environment, an improved adhesion force is provided and maintained.

According to an exemplary embodiment of the present disclosure, the sucker shape has a nanosize or a micro size. The sucker shape may be manufactured by a micro molding using an engraving mold, or by a liquid lithography using an incompatible liquid in an engraving mold. For example, a blotter space of the sucker may have a micro size, and a contact part of the sucker shape may have a nanosize and/or a micro size.

According to an exemplary embodiment of the present disclosure, the micro structure may have a size of about 1 µm to 100 µm, but the size of the micro structure is not limited thereto. For example, the micro structure may have a size of about 1 µm to 100 µm, a size of about 1 µm to 90 µm, a size of about 1 µm to 80 µm, a size of about 1 µm to 70 µm, a size of about 1 µm to 60 µm, a size of about 1 µm to 50 µm, a size of about 1 µm to 40 µm, a size of about 1 µm to 30 µm, a size of about 1 µm to 20 µm, a size of about 1 µm to 10 µm, a size of about 10 µm to 100 µm, a size of about 20 µm to 100 µm, a size of about 30 µm to 100 µm, a size of about 40 µm to 100 µm, a size of about 50 µm to 100 µm, a size of about 60 µm to 100 µm, a size of about 70 µm to 100 µm, a size of about 80 µm to 100 µm, or a size of about 90 µm to 100 µm, According to an exemplary embodiment of the present disclosure, the plurality of micro structures are arranged while spaced apart each other at an interval whose ratio with respect to a diameter of the sucker shape is within a range of 1:1 to 1:3. When the plurality of micro structures are arranged while spaced apart each other at an interval whose ratio with respect to a diameter of the sucker shape is within a range of 1:1 to 1:3 according to an exemplary embodiment of the present disclosure, a density of a contact surface can be increased.

According to an exemplary embodiment of the present disclosure, when a device is constructed by including the dry bonding system, a signal of the device may be amplified.

According to the second aspect of the present disclosure, there is provided a wearable device for skin bonding that includes a sensor part and a bonding part formed at an opposite side of the sensor part, the bonding part including the dry bonding system according to the first aspect of the present disclosure. The second aspect of the present disclosure includes the dry bonding system according to the first aspect of the present disclosure, and in the description of the second aspect of the present disclosure, descriptions identical to those of the first aspect will be omitted.

According to an exemplary embodiment of the present disclosure, the sensor part may be a sensor part to measure a resistance (a strain gauge) or a capacitance.

FIG. 5 is a schematic diagram illustrating a wearable device for skin bonding according to an exemplary embodiment of the present disclosure.

Referring to FIG. 5, a wearable device for skin bonding according to an exemplary embodiment of the present disclosure includes a sensor part 300 and a bonding part which is directly formed at the opposite side of the sensor part 300 by a micro molding or a liquid lithography and/or is bonded to the opposite side of the sensor part 300. The bonding part includes the micro structure 200 having a sucker shape formed on the substrate 100.

According to an exemplary embodiment of the present disclosure, the sensor part 300 may be provided in various types of sensors without limitation as long as it is generally used. The sensor part 300 may include a thin film patch type sensor, a resistance (a strain gauge) sensor and a capacitance sensor.

According to an exemplary embodiment of the present disclosure, the bonding part includes the dry bonding system according to the first aspect of the present disclosure, thereby providing a wearable device for skin bonding that may prevent skin from being irritated, humid and bleared even if attached to the skin for a long period of time and ensure a pleasant wear. In addition, the adhesion force of the bonding part is obtained by a van der Waals force, and even in a state of being wet with sweat or in a state of a high humidity, a sufficient adhesion force is provided.

According to an exemplary embodiment of the present disclosure, the bonding part is provided using the dry bonding system that operates based on a physical method without having a separate adhesive material, so that less skin irritation and easy attachment and detachment are provided compared to the existing wet bonding system that includes silicone-based adhesive material having a strong viscosity.

According to an exemplary embodiment of the present disclosure, the wearable device for skin bonding that is constructed by including the dry bonding system may amplify a signal of the wearable device. For example, the micro structure included in the dry bonding system may come into uniform and flexible contact with all parts of a skin surface regardless of unevenness or curvature of the skin surface, thereby achieving a signal sensitivity 10 times higher than that of the existing flexible device.

Hereinafter, an exemplary embodiment of the present disclosure will be described in detail. However, the present disclosure is not limited to the description.

EXAMPLES

1. Manufacturing of a Bonding System having an Embossed Sucker Structure

Referring to FIG. 6, a bonding system having an embossed sucker structure according to Example 1 of the present disclosure is manufactured by coating a silicone master mold having a hollow cylindrical engraved structure with a UV curable polymer material, for example, liquid PUA (or PDMS that is a UV curable polymer material), pressing a PET film against the coated polymer material by using a roller such that the polymer material permeates the entire area of the master mold, and then exposing the master mold to UV rays (or heat). Then, the cured polymer material is separated from the master molder. The polymer material is cured by UV rays (or heat) to form an inverse shape of the master mold (as shown in (d) of FIG. 6). The liquid polymer material, in the process of being coated on the master mold, is coated primarily on a surface of the master mold due to a difference in surface energy. In this case, the coating time is adjusted so as to manufacture a bonding system including an embossed sucker structure having a cavity structure in which a cylinder has a center portion thereof hollowed in the form of a sphere as shown in (a) of FIG. 7.

2. Manufacturing of a Bonding System Having an Engraved Sucker Structure

The bonding system having the embossed sucker structure manufactured in Example 1 is subject to the same pattern process as that performed in Example 1 one more time, thereby manufacturing a bonding system having an engraved sucker structure as shown in (b) of FIG. 7 (see (e) of FIG. 6).

3. A Bonding System Having a Solid Cylindrical Structure

In addition to using a master mold which has a hollow cylindrical groove that is manufactured through a semiconductor process, a bonding system having a solid cylindrical structure shown in (c) of FIG. 7 is manufactured by using the same patterning process that performed in Example 1.

4. A Bonding System Having a Hollow Cylindrical Structure

The bonding system having a solid cylindrical structure manufactured in Example 3 is subject to the same process as that performed in Example 3 one more time by using a UV curable polymer or thermally curable polymer, thereby manufacturing a bonding system having a hollow cylindrical structure as shown in (d) of FIG. 7.

Of the bonding system having an embossed sucker in a three dimensional structure according to Example 1 and the bonding system having an engraved sucker in a three dimensional structure according to Example 2, the bonding system having an embossed sucker structure exhibits a superior adhesion effect for a rough surface, such as human skin, and the bonding system having an engraved sucker structure exhibits a superior adhesion effect for a smooth surface, such as a silicone or glass substrate. These effects are attributed to a contact area that depends on a surface roughness.

COMPARATIVE EXAMPLE

1. A Bonding System Having a Flat Structure

A bonding system having a flat structure is manufactured as Comparative Example 1 with respect to the three dimensional bonding systems according to Examples 1 to 4.

Measurement of Perpendicular Adhesion Force

Referring to FIG. 8A, a force sensor and dry bonding parts provided at the opposite side of the force sensor according to Examples 1 to 4 and Comparative Example 1 are formed in order to test perpendicular adhesion forces of the bonding systems according to Examples 1 to 4 and Comparative Example 1. In addition, referring to FIG. 8B, a silicon wafer (a drawing on the left side of FIG. 8B) and pig skin (a drawing on the right side of FIG. 8B) are used as a bonding substrate.

First, in order to test a perpendicular adhesion force of a bonding system having an embossed sucker structure according to Example 1, the bonding system having an embossed sucker structure according to Example 1 is attached to pig skin that is similar to human skin. In this case, the pig skin has an oily membrane thereon. Referring to FIG. 9, the bonding system having an embossed sucker structure according to Example 1 has a superior perpendicular adhesion force compared to the bonding system having the solid cylinder structure according to Example 3 and the bonding system having a flat structure according to Comparative Example 1.

In order to test a perpendicular adhesion force of the bonding system having the engraved sucker structure according to Example 2 of the present disclosure at different humidity environments, the bonding system having the engraved sucker structure according to Example 2 is attached to a silicon wafer having a relative humidity of 45%, a silicon wafer having a relative humidity of 99% and a silicon wafer having water thereon. Referring to FIG. 10, even when the substrate has a significantly high relative humidity (99%), a superior perpendicular adhesion force is measured.

In addition, perpendicular adhesion forces according to different humidity environments are compared among the bonding system having an engraved sucker structure according to Example 2 of the present disclosure, the bonding system having a solid cylindrical structure according to Example 3 of the present disclosure, and the bonding system having a flat structure according to Comparative Example 1. Referring to FIGS. 11A to 11C, when the relative humidity is significantly high or water exists on the substrate, the bonding system having an engraved sucker structure according to Example 2 has a superior perpendicular adhesion force compared to Example 3 and Comparative Example 1.

Referring to FIGS. 9 to 11, the bonding systems including the embossed shape or engraved shape having a three dimensional structure according to Examples 1 and 2 of the present disclosure have superior perpendicular adhesion force even when a relative humidity is high or an oily membrane exists on the surface as well as in a dry condition. The superior adhesion force is attributed to a maximized contact area of a contact surface due to the three dimensional structure of the bonding system, and also to a suction effect obtained by a structure mimicking a sucker of mollusk, such as an octopus.

Measurement of a Perpendicular Adhesion Force According to Polymer Material and Bonding Substrate for Forming a Dry Bonding System The dry bonding systems according to Examples 1 to 4 are manufactured by using PUA, that is, a UV curable polymer material, and a silicon wafer is used as a bonding substrate, in order to measure a perpendicular adhesion force. Referring to FIG. 12A, the engraved structures (Examples 2 and 4 of the present disclosure) have a superior perpendicular adhesion force compared to the embossed structures (Examples 1 and 3 of the present disclosure). As a preload increases, the perpendicular adhesion force increases, and at a predetermined level, the perpendicular adhesion force is maintained without increasing. Such a behavior of the adhesion force is attributed to an adsorption effect caused by an empty space that is blocked from outside.

In addition, the dry bonding systems according to Examples 1 to 4 of the present disclosure are manufactured by using PDMS, that is, a thermally curable polymer material, and pig skin is used as a bonding substrate, so that perpendicular adhesion force is measured. Referring to FIG. 12B, similar to the result shown in FIG. 12A, the engraved structures (Examples 2 and 4 of the present disclosure) have a superior adhesion force compared to the embossed structures (Examples 1 and 3 of the present disclosure). As a preload increases, the perpendicular adhesion force increases, and at a predetermined level, the perpendicular adhesion force is maintained without increasing.

Referring to the experiments of FIGS. 12A and 12B, the silicon wafer having a smooth surface and the pig skin having a rough surface show approximately identical results. The superior adhesion force at the different bonding substrates is attributed to effective adsorption caused by using the polymer material having flexibility and elasticity.

Measurement of Perpendicular Adhesion Force According to Various Environment Conditions The dry bonding systems according to Examples 1 to 4 are manufactured by using PUA, that is, a UV curable polymer material, and a silicon wafer is used as a bonding substrate, in order to measure perpendicular adhesion forces according to various environment conditions. Referring to FIG. 13A, the bonding system having an engraved sucker structure (Example 2 of the present disclosure) mimicking a sucker structure of an octopus has an adhesion force that is rapidly increased under an environment condition having a high humidity or liquid. The increase in adhesive force is caused by a sucker structure mimicking a sucker of an octopus under the water that is able to easily adhere to various types of surfaces, in which a spherical protrusion included in a cylindrical hollow maximizes cohesion and adsorption effect with liquid.

In addition, the dry bonding systems according to Examples 1 to 4 and Comparative Example 1 are manufactured by using PDMS that is a thermally curable polymer material, and pig skin is used as a bonding substrate in order to measure perpendicular adhesion forces at various environment conditions. Referring to FIG. 13B, similar to the result obtained when using a UV curable material and a silicon wafer, when thermally curable material and pig skin are used, the engraved sucker structure mimicking a sucker structure of an octopus (Example 2 of the present disclosure) has a superior adhesion force at various environment conditions.

Measurement of a Wearable Device Including a Bonding System Including a Micro Structure Having a Sucker Structure A wearable device for skin bonding according to an exemplary embodiment of the present disclosure is manufactured by forming a dry bonding part including a micro structure having a three dimensional sucker structure at the opposite side of a sensor part through a liquid lithography. The wearable device for skin bonding and the dry bonding system according to an exemplary embodiment of the present disclosure do not additionally include a wet adhesive. An adhesion force of the device including the dry bonding part based on a micro structure having a three dimensional sucker structure according to an exemplary embodiment of the present disclosure is measured with respect to a skin or a rough surface. According to a result of the measurement, the adhesion force is equal to or superior to an adhesion force (3.5 N/cm$^2$) obtained by using the existing wet adhesive.

FIGS. 14A and 14B are graphs showing the signal amplification effect of a wearable device according to an exemplary embodiment of the present disclosure. Referring to FIG. 14B, a flexible device including a bonding system including a three-dimensional embossed shape or engraved shape according to an exemplary embodiment of the present disclosure allows a signal to be amplified over 10 times greater than a signal of the existing flexible device (see FIG.

14A). The signal amplification is attributed to a maximized contact area of a contact surface due to the three dimensional structure of the bonding system, and also to a superior suction effect obtained by a structure mimicking a sucker of mollusk, such as an octopus. It is expected that electrical signal amplification may be achieved at different humidity conditions.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

It will be apparent to those skilled in the art that various modifications can be made to the above-described exemplary embodiments of the present disclosure without departing from the spirit or scope of the invention. Thus, it is intended that the present disclosure covers all such modifications provided they come within the scope of the appended claims and their equivalents.

What is claimed is:

1. A bonding device, comprising:
   cylindrical micro structures each extending from a substrate and having a terminal end,
   wherein each of the micro structures includes a chamber extending into the terminal end, and
   wherein a diameter of an opening of the chamber at the terminal end is smaller than a diameter of the terminal end,
   wherein a protuberance extends from a floor of the chamber,
   wherein a circumference of a middle portion of the protuberance is larger than each of a circumference of an upper end of the protuberance and a circumference of a lower end of the protuberance, and
   wherein the circumference of the middle portion of the protuberance is smaller than a circumference of the chamber.

2. The bonding device of claim 1, wherein each of the micro structures includes a material selected from the group consisting of polyurethaneacrylate, polydimethylsiloxane, polyethyleneterephthalate, polyurethane, polyethylenenaphthalate, and a combination thereof.

3. The bonding device of claim 1, wherein the chamber is a sucker chamber.

4. The bonding device of claim 1, wherein the protuberance is spherical or semi-spherical.

5. The bonding device of claim 1, wherein the protuberance has a diameter of 1 μm to 100 μm and has a height of 1 μm to 100 μm, and an aspect ratio of the diameter to the height is within a range of ⅔ to 3.

6. The bonding device of claim 1, wherein adjacent micro structures among the micro structures are spaced apart from each other at an interval, and a ratio of the interval to a diameter the chamber is within a range of 1:1 to 1:3.

7. A wearable device for skin bonding comprising a sensor part and a bonding part provided at a side of the sensor part,
   wherein the bonding part includes the bonding device according to claim 1.

8. A skin bonding patch comprising the bonding device according to claim 1.

9. The skin bonding patch of claim 8, wherein the skin bonding patch includes a moist wound healing dressing.

10. A drug delivery bonding patch comprising the bonding device according to claim 1.

11. The drug delivery bonding patch of claim 10, wherein the bonding device includes a drug disposed in the chamber.

12. A bonding device, comprising:
    holes extending into a flat substrate; and
    a protuberance formed on a floor of each of the holes,
    wherein the protuberance has a height smaller than a depth of each of the holes,
    wherein a circumference of a middle portion of the protuberance is larger than each of a circumference of an upper end of the protuberance and a circumference of a lower end of the protuberance, and
    wherein the circumference of the middle portion of the protuberance is smaller than a circumference of each of the holes.

13. The bonding device of claim 12, wherein the protuberance is contained within each of the holes.

14. The bonding device of claim 12, wherein each of the holes has a diameter of 1 μm to 100 μm and has a height of 1 μm to 100 μm, and an aspect ratio of the diameter to the height is within a range of ⅔ to 3.

* * * * *